United States Patent [19]

Maier et al.

[11] Patent Number: 5,310,885
[45] Date of Patent: May 10, 1994

[54] PROCESS FOR IMMOBILIZING A PROTEIN CONTAINING SUBSTANCE ON A SOLID PHASE

[75] Inventors: Josef Maier, Weilheim; Dieter Mangold, Maxdorf; Reiner Schlipfenbacher, Lampertheim, all of Fed. Rep. of Germany

[73] Assignee: Boehringer Mannheim GmbH, Mannheim, Fed. Rep. of Germany

[21] Appl. No.: 887,239

[22] Filed: May 19, 1992

Related U.S. Application Data

[63] Continuation of Ser. No. 450,556, Dec. 14, 1989, abandoned.

[30] Foreign Application Priority Data

Dec. 19, 1988 [DE] Fed. Rep. of Germany ....... 3842700

[51] Int. Cl.⁵ .................. C07K 3/18; C07K 17/02; C07K 17/08; C07K 17/12
[52] U.S. Cl. .................. 530/413; 435/179; 436/528; 436/530; 530/362; 530/391.7; 530/403; 530/812; 530/813; 530/814; 530/815; 530/817
[58] Field of Search ........... 436/528, 535, 823, 530; 530/362, 369, 403, 413, 812, 813, 814, 815, 817, 391.7; 435/175, 178, 179

[56] References Cited

U.S. PATENT DOCUMENTS

| | | | |
|---|---|---|---|
| 4,004,979 | 1/1977 | Avrameas et al. | 530/812 |
| 4,066,512 | 1/1978 | Lai et al. | 435/175 |
| 4,081,329 | 3/1978 | Jaworek et al. | 530/813 |
| 4,338,398 | 7/1982 | Yoneyama | 435/179 |
| 4,410,634 | 10/1983 | Cooper et al. | 435/7.93 |
| 4,461,829 | 7/1984 | Greenquist | 436/530 |
| 4,742,158 | 5/1988 | Lehman et al. | 530/413 |
| 4,794,090 | 12/1988 | Parham et al. | 436/530 |
| 4,876,191 | 10/1989 | Hollander et al. | 435/178 |

FOREIGN PATENT DOCUMENTS

| | | |
|---|---|---|
| 0122209 | 10/1984 | European Pat. Off. |
| 0124320 | 11/1984 | European Pat. Off. |
| 0269092 | 6/1988 | European Pat. Off. |
| 1505400 | 3/1978 | United Kingdom |

OTHER PUBLICATIONS

Jastrzebski, *The Nature And Properties Of Engineering Materials*, 2nd ed. 1976, p. 386.
European Patent Application 88,695 (Sep. 14, 1983), p. 5.

*Primary Examiner*—Jeffrey E. Russel
*Attorney, Agent, or Firm*—Felfe & Lynch

[57] ABSTRACT

The present invention provides a process for immobilizing a protein or protein containing substance. The material to be immobilized is aggregated, contacted in a liquid with a hydrophilic solid phase and the solid phase, after contact has taken place, is dried. The present invention is also concerned with the solid phase prepared by this process and with the use thereof for analytical determination.

9 Claims, 2 Drawing Sheets

PROCESS FOR IMMOBILIZING A PROTEIN CONTAINING SUBSTANCE ON A SOLID PHASE

This application is a continuation of application Ser. No. 07/450,556, filed Dec. 14, 1989, now abandoned.

The present invention is concerned with a process for immobilizing proteins on a solid phase, the protein-carrying solid phase so prepared, and the use thereof.

Proteins immobilized on solid phases are of great importance in various fields of technology. Examples include the use of immobilized proteins in biotechnology, for example in bioreactors, and in biochemical production, for example for affinity chromatography.

Immobilized proteins have achieved particular importance in analysis, especially in analyses of parameters relevant for medical diagnosis using body fluids, such as blood, plasma, serum, urine, saliva, and the like. Bioaffinity reactions play an important part in these processes, employing those reactions in which a particular substance is specifically bound to a protein. Known substance/protein pairs which enter into such bioaffinity reactions include antigen/antibody, carbohydrate/lectin, biotin/avidin and the like. If the protein is immobilized on a solid phase, corresponding substances which are specifically bindable with the protein and are present in a sample are bound thereto and are removed from the sample and are determined qualitatively and/or quantitatively.

For example, for the detection of a partner of an antigen/antibody pair, heterogeneous immonoassays have been developed, many variants of which are known to the expert. It is common to all such processes that a partner of the antigen/antibody pair is bound to a solid phase. This immobilized partner is then used to carry out separation of at least a part of the corresponding binding partner from the sample. The amount of the binding partner separated off or the amount of the binding partner not separated off but remaining in the sample is then determined on a solid phase (separated portion) or in the remaining sample (not separated portion).

The prior art teaches a series of processes for immobilization of proteins on solid phases. Thus, the fixing of a protein on a solid phase can take place by chemical or physical means. Methods for the production of covalent bonds between a solid carrier material and proteins to be bound thereon have been known for a long time. For example, European Patent Specification No. 0,274,911 describes the use of chemically reactive synthetic resin membranes which are able to covalently bind proteins directly. However, this process for the production of protein-carrying solid phases requires a long contact time between the membrane and the protein to be bound in order to allow the chemical reaction to proceed to completion. Furthermore, active positions not saturated with protein must, in a subsequent step, be occupied with an inert protein in order that no more free membrane active positions are present which could negatively influence the use of the protein-laden solid phase at a later time.

Processes are known in which reactive groups of the solid phase are coupled with a bifunctional linker, where the remaining free functional group of the linker is covalently bound to the protein to be fixed. These processes require still more time and still more steps. However, with each process step, the risk increases that faulty batches will be produced, and the production costs also increase.

A problem of non-covalent fixing of proteins on a solid phase is the weaker binding which results. Thus, proteins which have been adsorbed from a solution onto a solid phase are relatively easily dissolved therefrom. Suggestions for overcoming this problem are known. U.S. Pat. No. 4,820,644 describes, for example, processes for fixing an immune-reactive material on a porous carrier material. In order to avoid problems of adhesion on the carrier material, the fixing is achieved by allowing an immune reaction to take place between the two partners of an immune reaction, i.e. between an antibody and an antigen or hapten. An immune complex mesh is formed which contains the protein to be bound (antibody or antigen) and this mesh binds on to the solid phase. The disadvantage of this fixing process is that, apart from the protein to be bound, expensive materials (antibody or antigen) are also needed. Furthermore, the preparation of the batch must be carried out with great precision in order to achieve optimum binding on the solid phase.

British Patent Specification No. 1,505,400, suggests cross-linking an immunologically active protein and then absorbing it on polystyrene latex particles, the adsorption being carried out in a latex emulsion. After the binding of a part of the protein on the latex particles, these are centrifuged off and washed several times. The protein-carrying polystyrene particles are stored as a suspension in buffered aqueous solutions and used for separation reactions.

European Patent Specification No. 0,122,209 describes a process for binding biological macromolecules on to solid phases which comprises polymerizing the macromolecules to be fixed, incubating for several hours together with hydrophobic carrier materials, for example polystyrene, and, after binding of a part of the polymerized macromolecules on to the carrier material, washing this several times before use or storage.

The two above-mentioned processes do not result in satisfactory adhesion of proteins, especially of specifically bindable substances to the carrier such as those which participate in bioaffinity reactions. Furthermore, time-consuming and laborious incubation and washing steps are necessary for fixing the protein on to the carrier. European Patent Specification No. 0,269,092 is concerned with a process for improving the adhesion in comparison with the two above-mentioned processes. For this process, the protein to be fixed is fixed covalently to a hydrophobic carrier protein and the complex obtained is adsorbed on a hydrophobic solid phase. By utilization of the hydrophobic exchange action between the solid phase and the carrier protein, an especially advantageous fixing is thereby achieved.

It is common to the three last-mentioned publications that hydrophobic carrier materials are used exclusively for the non-covalent fixing of proteins. This considerably limits the choice of carrier materials. In using protein-carrying solid phases in aqueous liquids, which includes all biological fluids, hydrophilic materials are often preferred because of their better wettability.

Starting from this prior art, it is an object of the present invention to bind proteins on to carrier materials which are substantially insoluble in water by means of a process which, even on a technical scale, is simple and quick to carry out in order to obtain protein-carrying solid phases which offer wide possibilities for use in the binding and possible separation of specifically bindable substances from liquid samples.

Thus, according to the present invention, there is provided a process for the immobilization of a protein on a solid phase, wherein the protein to be immobilized is aggregated, contacted in a liquid with a hydrophilic solid phase and the solid phase, after contact has taken place, is dried.

By means of the process according to the present invention, in principle all proteins can be immobilized which can be aggregated chemically or physically to higher molecular weights. By "chemical aggregation" is meant any process by which a chemical agent causes more than one molecule of the subject protein or protein containing molecule to be joined in an aggregate, thus causing a molecular weight increase. Thus for example, proteins can be aggregated by homopolymerization, for example by the addition of carbodiimides. However, they can also be joined or cross-linked with one another by means of polyfunctional molecules, such as so-called linkers. The palette of chemical linkers opens up the possibility of greater variability of the aggregates, for example with regard to the accessibility of particular protein positions, i.e., so-called "epitopes", to substances which are specifically bindable with the protein or with regard to the ability of the protein aggregate to adhere to the solid phase.

The method of cross-linking proteins by means of linkers is well known from the prior art. For example, British Patent Specification No. 1,505,400 and European Patent Specifications Nos. 0,122,209 and 0,269,092 describe such processes. For the process according to the present invention, linkers such as disuccinidyl suberate, S-aceteylmercaptosuccinic acid anhydride and maleinimidohexanoyl hydroxysuccinimide have proven to be advantageous. Disuccinidyl suberate is especially preferred according to the present invention for the aggregation of human albumin.

By physical aggregation is to be understood every molecular weight increase which is achieved without the use of chemical agents. For example, it is known to aggregate proteins thermally, for example albumin, and thus to increase the molecular weight thereof (see European Patent Specification No. 0,269,092). Thermally agrregated albumin is especially well suited for use in the invention.

When the prepared protein aggregate is to be lyophilized before its application to solid phase, for example for storage, it is recommended that a stabilizer be added to the aggregate before lyophilization, as is often the case in the lyophilization of protein solutions. This increases the storage stability of the lyophilized protein aggregate and its solubility when reconstituted with water or buffer. The nature and amount of these substances are dependent upon the nature of the particular protein. In general, those materials which may be added to the protein aggregate solution should not have a negative influence on the immobilization process or the bindability of the protein aggregate to the solid phase. Appropriate materials include, for example, saccharose, trehalose, mannose, dextrans and similar carbohydrates, as well as proteins such as crotein C, collagen and bovine serum albumin. Saccharose has proven to be particularly advantageous, especially in the case of human albumin cross-linked with disuccinidyl suberate. A typical concentration range for the stabilizers which may be added to the protein aggregate solution to be lyophilized and/or the solubilizing agents is 2 to 20% by weight. When saccharose is added to a solution of human albumin cross-linked with disuccinidyl suberate, the preferred concentration is from 4 to 10% by weight. When stabilizers and/or solubilizing agents are added to the protein aggregate solution to be lyophilized, care is to be taken that, the concentration thereof should not be so high that the bindability of the protein aggregate onto the solid phase is negatively influenced when a reconstituted lyophilizate is used. For example, when human albumin cross-linked with disuccinidyl suberate is to be immobilized, the concentration of saccharose in the protein aggregate solution should be less than 2% by weight.

"Proteins" and "protein containing molecules" as used herein includes not only naturally- occurring proteins and proteins isolated from natural sources but also synthetically prepared proteins. All can be immobilized in accordance with the described process. Examples of proteins which are preferred in the present invention include albumin, immunoglobulin (all types), transferrin and collagen. According to the present invention, protein containing molecules can also be fixed on to a solid phase. Biotin or a carbohydrate containing a protein are examples of these. According to the present invention, protein containing molecules can also be immobilized on solid phases.

The strength of the immobilization of the protein on the solid phase according to the present invention is dependent upon various factors. Among these are the particular protein to be fixed and the nature of the carrier material. With regard to the protein, it has been found that the adhesion to the solid phase increases with increasing molecular weight. No minimum size is necessary to achieve a particular binding strength, which depends upon the nature of the particular protein to be bound and can easily be determined. Thus, for example, in the case of albumin, an aggregate of 4 to 5 albumin units can be well immobilized in accordance with the present invention and an aggregate of at least 10 albumin units is especially advantageous.

Preferred solid phases according to the present invention are all those materials which are substantially insoluble in water and which are more hydrophilic than the aggregated protein to be immobilized. This implies that the solid phase after carrying the immobilized protein is more hydrophobic than the original solid phase. Appropriate materials include, for example, polyesters, sulphite cellulose, regenerated cellulose, linters, nitrocellulose, cellulose acetate and solid phases based on nylon. They can be present in any desired form, for example powders, grains, fibres, fleeces or films. Fleeces based on cellulose are specially preferred as solids in accordance with the present invention.

According to the process of the present invention, the aggregated protein is contacted in a liquid containing the solid phase. The aggregated protein is present in dissolved form, preferably in an aqueous liquid, such as a buffer solution. If a fleece is used as solid phase, it has proven to be especially advantageous to impregnate the fleece with a solution of the aggregated protein by dipping it into the solution so as to saturate it.

As buffer solutions, all buffers known not to damage the protein in question or its biological activity may be used. For example, for human albumin, phosphate or HEPES buffer with a pH value of from about 6 to about 9 and preferably of from about 7 to about 8 have proven to be especially useful.

To achieve good adhesion of the aggregated protein to the solid phase, it is important that, after contacting the protein aggregate with the solid phase, the solid phase carrying the protein is dried. "Drying" is to be understood as including all measures for removing as much liquid as possible. "Dry" as used herein refers to a hydrophilic solid phase with a residual moisture content of less than 7% by weight at 20° C. and 50% relative humidity. The residual moisture content below which "dry" is to be understood is, in the particular case, dependent upon the chosen solid phase. Thus, for example, cellulose fleece in the case of a residual moisture content of less than 7% by weight and a mixed fleece of cellulose and polyester fibers in a weight ratio of 50:50 of less than 5% by weight are to be called dry. In order to achieve such a degree of dryness in the case of hydrophilic solid phases in an economically acceptable drying time, as a rule, heat should be applied. Thus, according to the process of the present invention, the drying of protein-carrying fleece is preferably carried out at a temperature of from about 30° C. to about 80° C. If the length of drying time is not important, drying can also be carried out at ambient temperature in, for example, a current of air.

Surprisingly, it has been ascertained that the achievement of such a low residual moisture content of the solid phase carrying the protein is decisive for the excellent adhesion of the protein on the carrier. Higher residual moisture contents lead to weaker fixing of the protein on the solid phase.

The special advantage of the process according to the present invention lies in its simplicity. It suffices to dip the hydrophillic carrier material, such as hydrophilic fleece, in a solution of the aggregated protein to be fixed in order to saturate it with liquid. After impregnation has taken place, the carrier material is removed from the protein containing solution and dried. After drying, the protein aggregate is firmly bound to the solid phase. In this way, it is possible to achieve a homogeneous loading density of the solid phase with protein, the amount of immobilized protein thereby being known exactly.

The amount of protein which can be so bound to a solid phase is substantially higher than can be explained by adsorption. Thus, when after carrying out the process according to the present invention and after the drying, no protein can be eluted from the solid phase by an additional washing step, whereas without drying, i.e. when simple adsorption of the protein aggregate on the solid phase was carried out, the greater part of the adsorbed protein is eluted by washing. Therefore, according to the process of the present invention, a washing step is unnecessary when the concentration of the protein solution is chosen so that the total amount of protein in the solution is immobilized after the drying. This protein concentration is dependent upon the nature of the particular carrier material. The limiting concentration of protein which is completely immobilized can easily be determined by simple experiments.

A further advantage of the process according to the present invention is that the composition of the impregnation solution can be freely selected without disadvantageously influencing the binding properties of the protein to be immobilized. Thus, for example, the nature and concentration of the buffer, the pH value, ionic strength and possible stabilizers and/or stabilizers to be added can be selected, for the most part, solely according to the properties of the particular dissolved protein aggregate. This choice usually has no influence on the strength of the binding of the immobilized protein aggregate.

Solid phases produced by the process according to the present invention are very well suited for binding substances which are specifically bindable with the immobilized protein and thus for the removal of the binding substance from liquids. The most varied fields of use are conceivable, for example in biochemical production as carriers of immobilized proteins in bioreactors or for affinity chromatography for the enrichment and/or separation of specifically bindable substances.

Protein-carrying solid phases produced according to the present invention are especially preferred for analytical determinations of component materials in liquid samples. They are quite especially preferred for bioaffinity based determinations of component materials in body fluids such as blood, plasma, serum, urine, saliva and the like, as were described hereinbefore. For heterogeneous immunoassays, the protein-carrying solid phases according to the present invention are especially well suited, particularly for those which are carried out on a carrier such as a test strip.

DETAILED DESCRIPTION OF PREFERRED EMBODIMENTS

EXAMPLE 1

Figure 1:
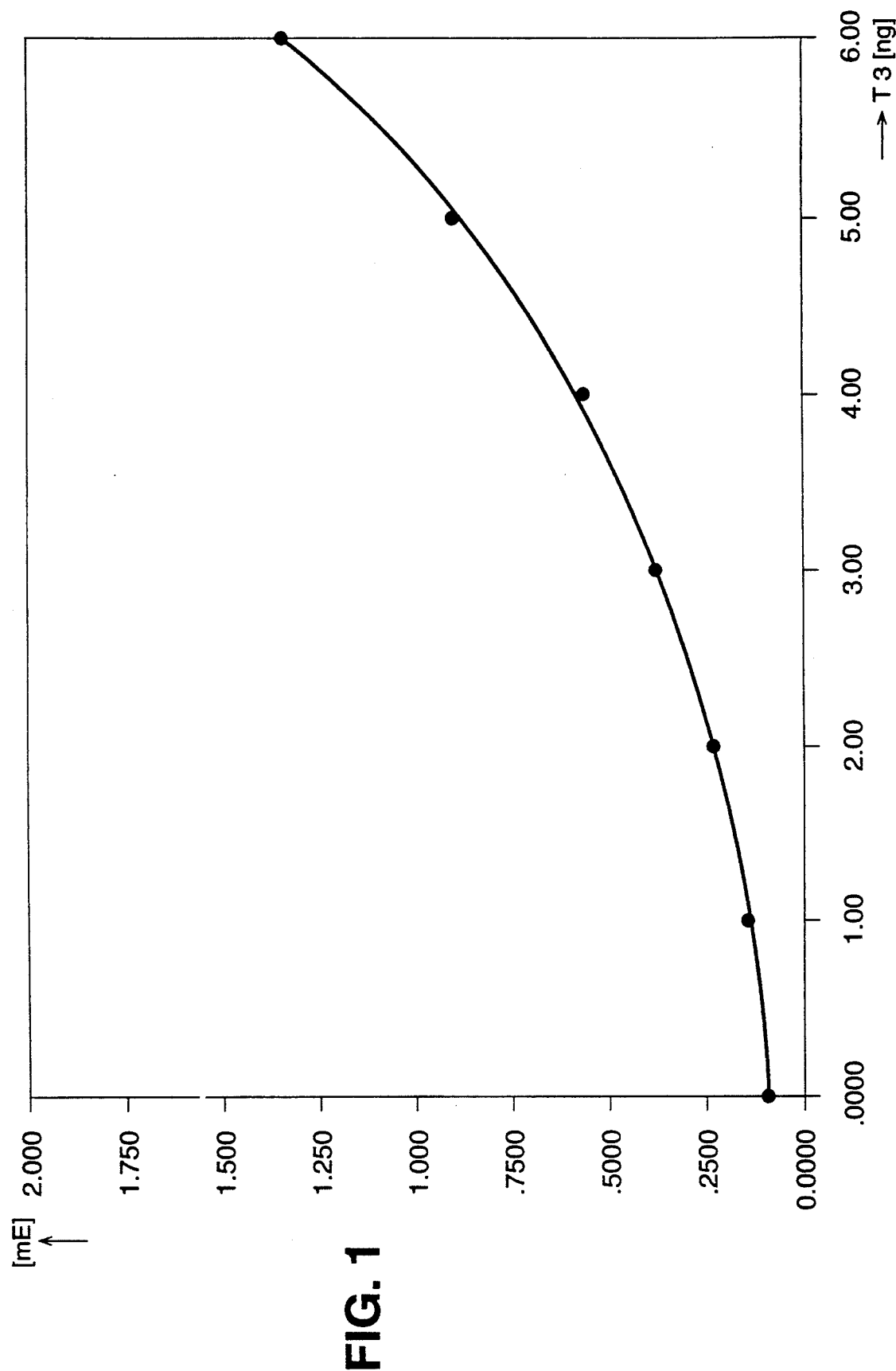
FIG. 1 is a standard, curve for T3 obtained using a solid carrier described herein.

Cross-linking of human serum albumin (HSA) by means of disuccinidyl suberate (DSS) to give poly-human serum albumin (pHSA)

1.5 g HSA is placed in 30 ml potassium phosphate buffer (200 mM; pH 8.0) and mixed within 2 hours with 2.5 ml of a solution of 50 mg DSS/ml dioxan. After completion of the cross-linking reaction, dialysis is carried out against a 500 fold volume of potassium phosphate buffer (20 mM, pH 7.2). The high molecular weight fraction (pHSA) with a molecular weight of more than 650,000 Dalton is separated on Superose 6 $^R$ (Pharmacia, Freiburg, Federal Republic of Germany) by gel filtration and, after the addition of 6 mg saccharose/mg of protein, is lyophilized.

EXAMPLE 2

Immobilization human serum albumin and comparison of the strength of adhesion of the immobilized protein with adsorbed protein 6×6 mm$^2$ sized and 0.5 mm thick pieces of fleece of 50% polyester/50% linters are impregnated with 15 μl of a solution of 250 mg/liter pHSA from Example 1 in 10 mM sodium phosphate buffer (pH 7.5) and a) dried for 30 minutes at 50° C. and washed three times with, in each case, 25 μl sodium phosphate buffer (10 mM, pH 7.5) in a centrifuge and subsequently centrifuged, or b) after 10 minutes, centrifuged in a centrifuge and washed twice with, in each case, 25 μl sodium phosphate buffer (10 mM, pH 7.5).

The wash centrifugates from a) and b) are, in each case, combined and, in each case, mixed with 300 mU anti-HSA-IgG-β-galactosidase conjugate (160 μl) and shaken for 10 minutes. Then, in each case, 200 μl are transferred into microtitre plate wells, the walls of which are loaded with HSA. After incubation for 1 hour, the wells are washed with phosphate-buffered physiological sodium chloride solution, developed with o-nitrophenylgalactoside and, after 10 minutes, the extinction is measured at 405 nm. The quantitative determination of the pHSA eluted from the fleece takes place by means of a calibration curve made at the same time.

The amount of pHSA with which each piece of fleece was contacted was 3.75 μg. After the elution, the following amounts were determined in the combined wash centrifugates:

| process | pHSA in the eluate | eluate referred to the impregnation solution |
|---------|--------------------|-----------------------------------------------|
| a) | 0.012 μg | 0.3% |
| b) | 2.64 μg | 71% |

The protein immobilized according to the present invention is, because of the drying step, substantially more firmly bound to the solid phase than the solely adsorbed protein which for the most part, can be washed out from the solid phase.

EXAMPLE 3 a) Preparation and cross-linking of rabbit IgG-T3 conjugate 3 g Rabbit IgG are dissolved in 300 ml potassium phosphate buffer (100 mM, pH 8.5) and mixed with a solution of 58 mg N-tert-butyloxycarbonyltriiodothyronine N'-hydroxysuccinimide ester (BOC-T3-N'-hydroxysuccinimide ester) in 30 ml dioxan. After a reaction time of 2 hours, the protein solution is dialyzed against a 200 fold volume of 20 mM potassium phosphate buffer (pH 7.8) and adjusted via ultra-filtration (Amicon YM 100 ® membrane) to a concentration of 50 mg/ml.

For the cross-linking, 35 ml disuccinidyl suberate (concentration 10 mg disuccinidyl suberate/ml dioxan) is slowly added to the batch. After completion of the cross-linking reaction, dialysis is carried out against a 500 fold volume of potassium phosphate buffer (50 mM, pH 7.2). The fraction eluted on Superose 6 R in the exclusion volume is separated off, stabilized with saccharose (concentration 6 mg saccharose/mg IgG) and lyophilized.

b) Triiodothyronine (T3) test

A fleece of 60% sulphite cellulose and 40% linters is impregnated with cross-linked rabbit IgG-T3 conjugate from Example 3a) in a concentration of 250 μg/ml in 50 mM potassium phosphate buffer (pH 7.2) and, after complete saturation, dried at 50° C. for 60 minutes in a circulating air cabinet. In each case, 50 μl of sheep anti-T3-IgG-β-galactosidase conjugate (prepared analogously to the process described in J. Immunoassay, 4, 209–327/1983)(120 mU in phosphate-buffered physiological sodium chloride solution, 5 g/liter bovine serum albumin) are incubated for 5 minutes with 50 μl of a T3 standard series and subsequently pipetted on to the above produced pieces of fleece (8×8 mm, thickness 0.5 mm) of the T3 matrix. After an incubation time of 5 minutes, the pieces of fleece are centrifuged and the β-galactosidase activity of the filtrate determined with 40 mM chlorophenol red galactoside solution (prepared according to U.S. Pat. No. 4,668,622) at 578 nm.

The standard curve illustrated in FIG. 1 is obtained. This can be used for the examination of solutions with unknown T3 content.

EXAMPLE 4

Preparation and cross-linking of rabbit IgG-digoxigenin conjugate a) 3 g Rabbit IgG are dissolved in 300 ml potassium phosphate buffer (100 mM, pH 8.5) and mixed with a solution of 58 mg digoxigenin(3-succinidyl)-N-hydroxysuccinimide in 30 ml dioxan. After a reaction time of 2 hours, the protein solution is dialyzed against a 200 fold volume of 20 mM potassium phosphate buffer (pH 7.0) and adjusted via ultra-filtration (Amicon YM 100 ® membrane) to a concentration of 50 mg/ml.

For the cross-linking, 35 ml disuccinidyl suberate solution (concentration 10 mg disuccinidyl suberate/ml dioxan) are slowly added to the batch. After completion of the cross-linking reaction, dialysis is carried out against a 500 fold volume of potassium phosphate buffer (50 mM, pH 7.2). The fraction eluted on Superose 6 ® in the exclusion volume is separated off, stabilized with saccharose (concentration 6 mg saccharose/mg IgG) and lyophilized.

b) Digoxin Test

A fleece of 60% sulphite cellulose and 40% linters is impregnated to saturation with cross-linked rabbit IgG-digoxigenin conjugate from Example 4a) (250 μg/ml in 50 mM potassium phosphate buffer, pH 7.2) and dried at 50° C. for 60 minutes in a circulating air cabinet.

In each case, 50 ul sheep anti-digoxin-IgG-β-galactosidase conjugate (prepared analogously to the process described in J. Immunoassay, 4, 209–327/1983) (120 mU in phosphate-buffered physiological sodium chloride solution, 5 g/liter bovine serum albumin) are incubated for 5 minutes with 50 ul of a digoxin standard series and subsequently pipetted on to the above-prepared pieces of fleece (8×8 mm, thickness 0.5 mm) of the digoxin matrix. After an incubation time of 5 minutes, the pieces of fleece are, in each case, centrifuged off in a centrifuge and the β-galactosidase activity of the centrifuge determined with 40 mM chlorophenol red galactoside solution (prepared according to U.S. Pat. No. 4,668,622) at 578 nm.

Figure 2:
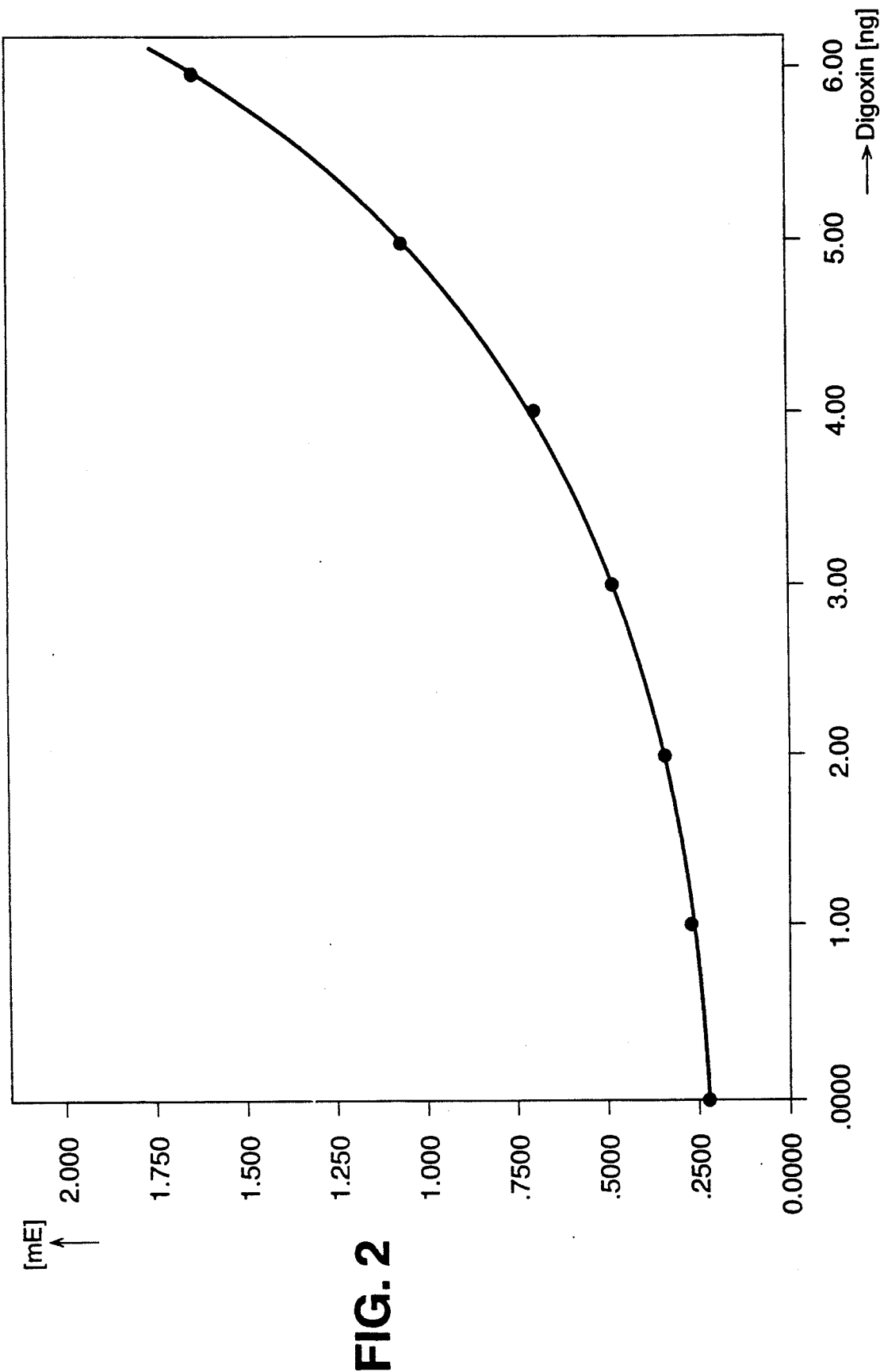
FIG. 2 is a standard curve for digoxin obtained using a solid carrier described herein.

The standard curve shown in FIG. 2 of the accompanying drawings is obtained, by means of which the unknown digoxin content is a solution can be determined.

EXAMPLE 5

Impregnation of paper with thermally aggregated bovine serum albumin-streptavidin conjugate (tBSA-SA) and determination of the desorption rate

1. Impregnation 8 mm×8 mm square of paper (80% polyester/20% cellulose/20% (referred to fibers) Etadurin) are impregnated with 42 μl of a solution of 0.5 μg/ul tBSA-SA (Boehringer Mannheim GmbH, Mannheim, Bundesrepublik Deutschland) in 50 mMol/l potassium phosphate buffer, pH 7.0. The impregnated paper is dried for 30 minutes at 70° C.

2. Determination of the desorption rate

An impregnated fleece according to step 1 is vortexed for 15 minutes in 1 ml of 50 mM potassium phosphate buffer, pH 7.0. The supernatant is transferred to a 1 ml enzymun-plastic tube (Boehringer Mannheim GmbH, Mannheim, Bundesrebublik Deutschland), which is internally precoated with 1 μg/ml tBSA-Biotin 1:1 (Boehringer Mannheim GmbH, Mannheim, Bundesrepublik Deutschland) and incubated for one hour. After washing twice with water 1 ml of a solution of peroxidase-biotin-conjugate (20 mU/ml, Boehringer Mannnheim GmbH, Mannheim, Bundesrepublik Deutschland) is added into the tube and is incubated there for 30 minutes. After washing twice with water 2,2'-azino-di[3-ethylbenzthiazolinisul- fonate] is added into the tube and the reaction solution is measured at 405 nm. The system is calibrated with a set of tBSA-SA-solutions of known concentration.

When using the impregnated paper according to step 1, 18 ng tBSA-SA are desorbed, which is equal to 0.09%. When omitting the drying step in the impregnation procedure according to step 1 560 ng tBSA-SA are desorbed which is equivalent to 2.7%. One concludes, therefore, that protein immobilized according to the present invention is essentially firmer bound to the solid phase than the solely adsorbed protein.

It will be understood that the specification and examples are illustrative but not limitative of the present invention and that other embodiments within the spirit and scope of the invention will suggest themselves to those skilled in the art.

We claim:

1. Process for immobilizing a protein containing substance onto a solid phase comprising:
   (i) forming a water soluble aggregate of a polymer containing more than one molecule of a particular protein;
   (ii) contacting a liquid containing said aggregate in dissolved form with a hydrophilic solid phase so as to adsorptively, and non-covalently bind said aggregate to said hydrophilic solid phase; and
   (iii) drying said solid phase to form a solid phase having said aggregate immobilized and non-covalently bound thereon.

2. Process of claim 1, wherein said forming of said water soluble aggregate comprises mixing more than one molecule of a particular protein with a polyfunctional linker.

3. Process of claim 1, wherein said drying comprises treating said solid phase to contain less than 7% moisture by weight at 20° C. and 50% relative humidity.

4. Solid phase having protein bound thereto comprising a hydrophilic solid phase having non-covalently bound thereto a protein aggregate, wherein said aggregate is formed by aggregating more than one molecule of a particular protein to form a polymer containing aggregate prior to contacting said aggregate with said solid phase, wherein said solid phase is dried following contact of said solid phase with said polymer containing aggregate.

5. Solid phase of claim 4, wherein said solid phase is characterized by a moisture content of less than 7% by weight at 20° C. and 50% relative humidity.

6. Method for determining an analyte in a liquid sample, comprising contacting said liquid sample with the protein aggregate containing solid phase of claim 5, wherein said aggregate comprises a substance which binds with said analyte and determining said analyte bound to said aggregate.

7. Process for immobilizing a protein containing substance onto a solid phase comprising:
   (i) forming a water soluble protein homopolymer aggregate;
   (ii) contacting a liquid containing said protein homopolymer aggregate in dissolved form with a hydrophilic solid phase so as to adsorptively, and non-covalently bind said protein homopolymer aggregate to said hydrophilic solid phase; and
   (iii) drying said solid phase to form a solid phase having said protein homopolymer aggregate immobilized and non-covalently bound thereon.

8. Solid phase having protein bound thereto comprising a hydrophilic solid phase having non-covalently bound thereto a protein homopolymer aggregate, wherein said homopolymer aggregate is formed prior to contacting said homopolymer aggregate to said solid phase, wherein said solid phase is dried following contact of said solid phase with said homopolymer aggregate.

9. Solid phase having protein bound thereto comprising a hydrophilic solid phase having non-covalently bound thereto a protein aggregate, wherein said aggregate is formed by mixing more than one molecule of a particular protein with a polyfunctional linker to form a protein containing aggregate prior to contacting said protein aggregate with said hydrophilic solid phase, wherein said solid phase is dried following contact of said solid phase with said protein aggregate.

* * * * *